United States Patent [19]

Simpson

[11] Plant 4,146

[45] Nov. 8, 1977

[54] *ILEX VERTICILLATA* BUSH NAMED WINTER RED

[76] Inventor: Robert C. Simpson, 1504 Wheatland Road, Vincennes, Ind. 47591

[21] Appl. No.: 746,477

[22] Filed: Dec. 1, 1976

[51] Int. Cl.[2] ..... A01H 5/00

[52] U.S. Cl. ..... Plt./65

*Primary Examiner*—Robert E. Bagwill

*Attorney, Agent, or Firm*—William A. Snow; Charles W. Rummler

[57] ABSTRACT

A new variety of *Ilex verticillata* bush characterized by the brilliant coloring of the abundant fruit and coloring and retention of brilliant fruit or berry long after other plants of the species have faded or discolored. The hybrid is sterile.

1 Drawing Figure

BACKGROUND OF THE INVENTION

My new variety of *Ilex verticillata* is a deciduous shrub and was discovered by me at Vincennes, Ind., in a cultivated area. Propagation of this new plant by soft wood cuttings has been carried out by me and on my behalf at Cunningham Gardens, Waldron, Ind., Gulf Stream Nursery at Wachapreague, Va., and at Cully Nursery, Jacksonville, Ill., through several generations and all of the scions hold true from generation to generation.

DESCRIPTION OF THE DRAWING

My new variety of *Ilex verticillata* is illustrated by the accompanying photographic drawing.

DESCRIPTION OF THE NEW PLANT

The following is a description of the new variety of *Ilex verticillata* with color designation according to The RHS Colour Chart of The Royal Horticultural Society.

THE PLANT

Origin: Seedling.
Parentage:
*Seed parent.*—Unknown.
*Pollen parent.*—Unknown.
Botanical name: *Ilex verticillata.*
Commercial name: Black Haw or Michigan Holly.
Form: Bush (typical of species). Shape: Rounded.
Height: 5 to 8 feet.
Growth rate: Medium.
Trunk size: Multiple stem.
*Bark.*—Dark Olive Brown.
Branches: Angle of attachment — 30°-40°.
*Size.*—Slender.
*Bark.*—Dark Olive Brown.
Leaves:
*Length.*—3 to 5 inches.
*Width.*—1½ to 1¾ inches.
*Margin type.*—Crenate, smooth.
Pubescence distribution.—Under side of leaf and ribs.
*Quantity.*—Dense.
*Color.*—Upper side — Medium Green; under side — somewhat lighter.
*Leaflets.*—None.
*Petioles.*—Length — ½ inch.
*Thorns.*—None.
*Spines.*—None.
*Prickles.*—None.

FLOWER BUDS

Size: Very small, with 5 tiny petals.
Form: Ovoid.
Color:
*When sepals first divide.*—White.
*When sepals begin to unfurl.*—White.

FLOWERS

Blooming period: June 10 to 25.
Quantity: Profuse.
Size: Small.
Diameter: ¼ inch in a cluster.
Shape: Flat; does not change later.
Petalage: Arrangement — imbricate.
Peduncle:
*Length.*—1/16 inch.
*Color.*—Green.
Fragrance: None.

REPRODUCTIVE ORGANS

Pollen: Color — none; female.
Stamen: Sterile.
Ovaries: Typical of species.

FRUIT

Maturity period: October, color lasting through March.
Size: Uniform, small and spherical.
Axial Diameter: ¼ inch.
Transverse diameter: ¼ inch.
Skin:
*Texture.*—Smooth.
*Lenticels.*—None.
*Color.*—Bright Red, Plate 44A.
*Markings.*—None.

This new variety has more brilliance in its fruit and abundance of fruit massed on the twigs. One of the primary characteristics is the retention of brilliant fruit color long after other plants of the species have faded or discolored, or lost all fruit color and turned black. The brilliance frequently lasts until spring.

The fruit of this new variety is typical for the species except for its brilliant red color, abundance, and long lasting qualities having been under observation at several widely separate locations.

I claim:

1. A new and distinct variety of *Ilex verticillata* plant as herein shown and described, characterized by abundant fruit and the retention of the brilliant red fruit coloration, retaining this characteristic from October through March, its easy propagation from cuttings, and its vigorous growth habit.

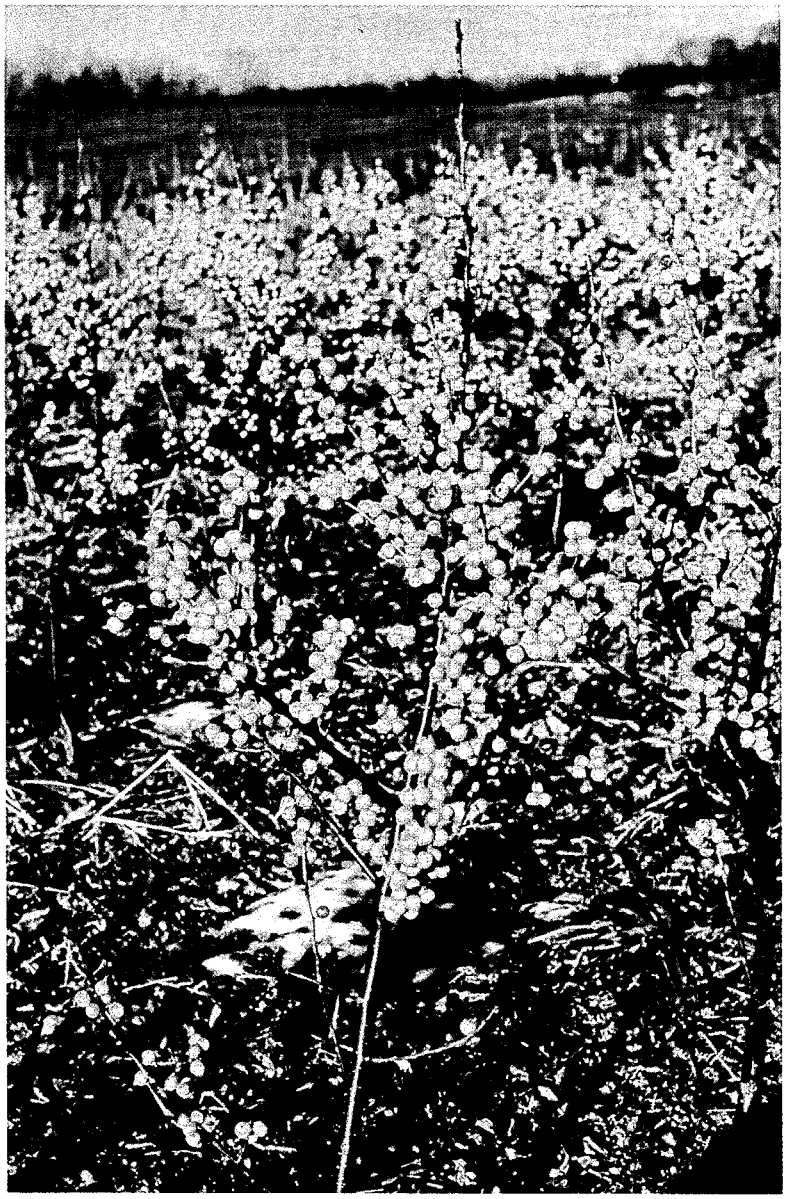

* * * * *